(12) United States Patent
Barnett et al.

(10) Patent No.: US 6,593,085 B1
(45) Date of Patent: Jul. 15, 2003

(54) ASSAY METHOD AND APPARATUS (75) Inventors: Graeme Ross Barnett, Shailer Park (AU); Roy L. Manns, Rockland, MA (US)

(73) Assignee: Panbio Pty Ltd (AU)

( * ) Notice: Subject to any disclaimer, the term of this patent is extended or adjusted under 35 U.S.C. 154(b) by 0 days.

(21) Appl. No.: 09/582,160

(22) PCT Filed: Dec. 17, 1998

(86) PCT No.: PCT/AU98/01038

§ 371 (c)(1),
(2), (4) Date: Nov. 13, 2000

(87) PCT Pub. No.: WO99/32885

PCT Pub. Date: Jul. 1, 1999

(30) Foreign Application Priority Data

Dec. 19, 1997 (AU) .............................................. PP1034

(51) Int. Cl.[7] ............................................ G01N 33/533
(52) U.S. Cl. ............................ 435/6; 435/7.1; 435/7.5; 435/7.9; 435/7.92; 435/7.93; 435/7.94; 435/7.95; 436/512; 436/513; 436/514; 436/518; 436/528; 436/532; 436/540; 436/541; 436/823
(58) Field of Search ............................ 435/7.1, 7.5, 7.9, 435/7.92–7.95, 6; 436/512, 513, 514, 518, 528, 532, 540, 541, 823

(56) References Cited

U.S. PATENT DOCUMENTS

| | | | |
|---|---|---|---|
| 4,632,901 A | 12/1986 | Valkirs et al. | |
| 4,877,586 A | 10/1989 | Devaney, Jr. et al. | |
| 4,943,522 A | 7/1990 | Eisinger et al. | |
| 5,354,692 A | 10/1994 | Yang et al. | |
| 5,401,667 A | 3/1995 | Koike | |
| 5,565,366 A | 10/1996 | Akers, Jr. | |
| 5,607,863 A | 3/1997 | Chandler | |
| 5,725,774 A | 3/1998 | Neyer | |
| 5,762,871 A | 6/1998 | Neyer | |
| 5,772,966 A | 6/1998 | Maracas et al. | |
| 5,789,165 A | 8/1998 | Oku et al. | |
| 5,905,038 A | 5/1999 | Parton | |
| 5,916,521 A | 6/1999 | Bunce et al. | |
| 6,054,100 A | 4/2000 | Stanchfield et al. | |
| 6,054,325 A | 4/2000 | Kedar et al. | |
| 6,083,761 A | 7/2000 | Kedar et al. | |
| 6,303,325 B1 | * 10/2001 | Mehta et al. | |
| 6,342,396 B1 | * 1/2002 | Perrin et al. | |

FOREIGN PATENT DOCUMENTS

| | | |
|---|---|---|
| EP | 0 201 079 | 11/1986 |
| EP | 0 507 586 A2 | 10/1992 |
| EP | 0 905 517 A1 | 2/1996 |
| WO | WO 95/24649 | 9/1995 |
| WO | WO 96/10179 | 4/1996 |
| WO | WO 97/06439 | 2/1997 |

* cited by examiner

Primary Examiner—Bao-Thuy L. Nguyen
(74) Attorney, Agent, or Firm—Knobbe, Martens, Olson & Bear, LLP (57) ABSTRACT

A method of assaying for an analyte including the steps of: (i) passing a sample suspected of containing an analyte and reagents comprising a target ligand-analyte receptor conjugate and a detectable tracer containing a label for the analyte through filter apparatus containing a plurality of discrete flow zones wherein at least one zone functions as a capture zone having bonded thereto a receptor ligand for said target ligand; (ii) allowing the sample and accompanying reagents to incubate prior to passage through said at least one zone to facilitate formation of complex(es) of said conjugate and said at least one analyte in a liquid or fluid phase; and (iii) detecting the presence of analyte in the sample by activation of the label in said at least one zone after binding of the complex(es) conjugate to the associated receptor ligand(s).

18 Claims, 8 Drawing Sheets

ASSAY METHOD AND APPARATUS

FIELD OF THE INVENTION

THIS INVENTION relates to an assay method and apparatus suitable for determination of analyte wherein assay apparatus is provided having one or multiple capture zones incorporating a receptor ligand for detection of analyte.

BACKGROUND OF THE INVENTION

Lateral flow membranes for immunoassays are well known and reference may be made, for example, to U.S. Pat. No. 4,943,522 which refers to a porous membrane capable of non-bibulous lateral flow which is used as an assay substrate. A member of a binding pair is affixed in an indicator zone defined in the substrate. A sample is applied at a position distant from the indicator zone and permitted to flow laterally through the zone. Any analyte in the sample is complexed by the affixed binding partner and detected. A method of detection employs entrapment of observable particles in the complex.

Another lateral flow assay is described in U.S. Pat. No. 5,798,273 wherein the presence or amount of an analyte in a sample may be determined by contacting a sample with anti-analyte antibodies which bind to the analyte or to both analyte and an analyte analog and an assay tracer prior to application to a lateral flow device. A first member of a binding pair is incorporated with the tracer. The lateral flow device comprises a solid support having a sample addition area, a capture area containing analyte or analyte analog which is immobilized thereon and a read out area comprising one or a plurality of zones having a second member for the binding pair immobilized thereon which binds with the first member to detect the presence or amount of analyte in the sample.

Lateral flow type assays are also described in European Patent No. EP0291194 which refers to a casing having a dry porous carrier. A liquid test sample may be applied to the dry porous carrier which has a labelled specific binding reagent for an analyte which reagent is freely movable within the porous carrier when in the moist state and unlabelled specific binding reagent for the same analyte which is immobilized in a detection zone on the porous carrier. The liquid sample may pick up labelled reagent and thereafter permeate to the detection zone. The label used is a particulate direct label.

Reference may also be made to lateral flow assay devices which are described in U.S. Pat. Nos. 5,607,863, 5,648,274 and 5,468,648 which each refer to devices having a first opposable component and a second opposable component wherein at least one of the opposable components comprises capture and detection zones and at least one of the opposable components includes an absorber for contacting the other of the opposable components for detection of analyte. Each of these references describe capture zones which incorporate specific binding partners for the analyte. U.S. Pat. No. 5,468,648 describes provision of a test strip that can carry out multiple assays simultaneously.

Reference may also be made to U.S. Pat. Nos. 5,401,667, 4,855,240, 5,602,037, 5,712,170 and 4,727,019 which all refer to complicated forms of lateral flow assay devices and each of which incorporates capture zones for capture reagent or receptor to bind directly to analyte in a sample being tested.

Reference may also be made to U.S. Pat. No. 5,185,127 which refers to a vertical filter stack in an enclosure having a base portion and a lid. The filter stack has an initial hydrophilic membrane having a binder for analyte thereon, a hydrophobic membrane under the hydrophilic membrane and a pad of absorbent material under the hydrophobic membrane.

Reference may also be made to the following references which use a lateral flow device described above in U.S. Pat. No. 5,468,648, i.e.:

(i) Chew et al., 1998, Clin. Diagn. Lab. Immunol. 5 407–409;

(ii) Vaughn et al., 1998, J. Clin. Micro. 36 234–238;

(iii) Lam et al., 1998, J. Clin. Virol. 10 75–81;

(iv) Cuzzubbo et al.., Jan/Mar 1998, Singapore Microbiologist, 16–17; and (v) Devine et al., 1998, Analytical Testing Technology 15 16.

As is clear from the prior art referred to above, a feature of such prior art is the provision of lateral flow devices or filter stacks which include one or a plurality of capture zones for direct binding of analyte for detection of the analyte.

However, it has now been realised that such prior art devices have several disadvantages, the most notable of which is the following:

(i) by employing capture zones having a specific binding agent for the analyte, it will be appreciated that such binding agents, which are usually proteins, may in some cases comprise unstable biological material that is usually incapable of being stored at room temperature;

(ii) by virtue of (i), it is usual that such prior art devices can only be used once and therefore must be discarded;

(iii) only relatively small volumes of sample and accompanying reagents can be accommodated due to the necessity for controlling the flow of sample and accompanying reagents through the prior art device to relatively slow speeds;

(iv) often accumulation of complexes occur both in the capture zones and non-capture zones restricting the flow of sample and reagents through the prior art device;

(v) often non-specific reactions and aggregation of reactants may cause non-specific binding; and (vi) serious limitations apply to processing detection of multiple analytes in prior art devices. For example, when detection of both multiple specificities of IgG and IgM classes of antibodies is being attempted, it is not possible to use anti-IgG or anti-IgM receptors in the capture zones or antigens specific to IgG or IgM antibodies because of the danger of cross reactions occurring, preventing the differentiation between antibody specificity and immunoglobulin class.

SUMMARY OF THE INVENTION

It is therefore an object of the invention to provide an assay method to reduce the affect of the abovementioned disadvantages.

It is a further object of the invention to provide an assay apparatus which is of simple construction and which can be used for assaying a number of different analytes simultaneously.

In accordance with the invention, there is provided a method of assaying for an analyte including the steps of:

(i) mixing a liquid sample suspected of containing an analyte and reagents comprising a target ligand analyte receptor conjugate and a detectable tracer containing a label for the analyte whereby if the analyte is present, there is formed in solution a complex of analyte coupled to the conjugate after incubation of the mixture;

(ii) passing the mixture through filter apparatus containing a plurality of discrete flow zones wherein at least one zone functions as a capture zone having bonded thereto a receptor ligand for the target ligand;

(iii) detecting the presence of analyte in the sample by activation of the label in said at least one zone after binding of the complex to the receptor ligand; and (iv) continuing the passage of the mixture past said at least one zone to a wicking zone for liquid entrapment.

Thus, one of the principal features of the present invention is that any analyte complex(es) involving the target ligand-analyte receptor conjugate are formed in a liquid or fluid phase prior to retention on a capture zone when the complex (es) bind to associated receptor ligand(s).

The above method is especially adapted for assaying a number of different analytes simultaneously. To this end, the assay apparatus may have a plurality of capture zones which have a different receptor ligand bonded thereto. The sample in step (i) may also be combined with a target ligand-analyte receptor conjugate specific for each analyte being assayed and a detectable tracer incorporating a label for each analyte. In this embodiment, step (ii) facilitates the activation of each analyte by detection of the label in each zone after bonding of each complex to its associated receptor ligand.

The method of the invention may be used for detection of a wide variety of different analytes. In this regard, it will be appreciated that the term "analyte" refers to any compound or composition to be detected that is capable of binding specifically to a binding agent. Examples of binding agents are antibodies, antigens or chelating agents or receptor ligands discussed hereinafter.

The term "analyte" may also include within its scope analyte analogs as referred to in U.S. Pat. No. 5,624,809 which is herein incorporated by reference in its entirety.

Analytes may have a simple binding site (i.e. monovalent) or multiple binding sites (i.e. polyvalent). Polyvalent analytes may comprise polymers inclusive of polypeptides, proteins, polysaccharides, nucleic acids or combinations thereof.

Analytes may also include mono-epitopic liquid species, such as drugs, metabolites, pesticides and pollutants.

Examples of a wide variety of analytes to which the invention is relevant are mentioned in U.S. Pat. Nos. 4,943, 522 and 5,624,809, both of which are incorporated herein by reference.

Other analytes include immunoglobulins IgA, IgG, IgE and IgM, enzymes and receptors inclusive of nucleic acids and proteins as described in U.S. Pat. No. 5,624,809.

The term "tracer" as made herein may comprise any suitable binding partner specific for analyte(s) of interest contained in a sample being tested. A convenient form of tracer is an antibody specific for an antigen when the analyte of interest. The label may be any conventional marker which after binding of the analyte to the tracer provides a detectable signal. Examples of labels may be a radioactive species, fluorescent species, chemiluminescent species or an enzyme for which a substrate convertible to a coloured product exists such as a peroxidase or alkaline phosphatase. Examples of appropriate tracers or labels are referred to in U.S. Pat. No. 5,208,143, which is herein incorporated by reference, or U.S. Pat. No. 5,624,809 supra.

The preferred label in relation to the present invention is colloidal gold which may be conjugated to antibody or paratope thereof or antigen or epitope thereof. Also may be used as labels are coloured microparticles, coloured dendrimers or coloured dendrimer type molecules.

The term "receptor ligand" as used herein refers to any species which may be immobilized or bound to a filter zone or flow zone and which is a specific binding partner for a "target ligand". Examples of receptor ligands are antibodies, antigens including haptens, dendrimers, dendrimetric type molecules, oligomers comprising a sequence of monomers selected from the group consisting of amino acids, carbamates, sulfones, sulfoxides, nucleotides, carbohydrates, ureas, phosphonates, liquids, esters or combination thereof or any other molecule or composition capable of recognizing a particular site of a molecule which may be an epitopic or determinant site. Naturally occurring receptor ligands also include nucleic acids, metal chelates, enzymes, biotin, lectins, oligonucleotides and peptides. Dendrimers or dendrimeric-type molecules may also be used as receptor ligands.

The term "target ligand" as used herein refers specifically to the specific binding partner to the "receptor ligand" and thus may include any of the species discussed above for the receptor ligand. It will also be appreciated that the "target ligand" may also be bound to a specific carrier such as dendrimers, microparticles, latex beads, dendrimers, dendrimeric-type molecules, branched polymers, zeolites, fullerenes, streptavidin, avidin or other substance capable of conjugation to the target ligand.

The microparticles when used as carriers may be of any convenient size that are suitably small enough that they may form a suspension in aqueous solution to facilitate their coating with an antibody, antigen, oligonucleotide or any of the species discussed above for the receptor ligand or target ligand. The average individual size of the microparticles is about 0.01–50 microns, more preferably 1–10 microns. The microparticles can be selected from any suitable type of particulate material, such as polystyrene, polymethylacrylate, polypropylene, silica, teflon, fluropolymers, latex, polytetrafluoroethylene, polyacrylanitrile or polycarbonate.

Reference may also be made to Australian Patent Application Nos. 22431/95 or 22889/95 in the name of Dade International, Inc. or U.S. Pat. No. 5,714,166 for the types of dendrimers that may be used as carriers. Therefore, Australian Patent Application Nos. 22431/95 and 22889/95 and U.S. Pat. No. 5,714,166 are incorporated herein by reference.

The attachment between the receptor ligand and the target ligand may utilize covalent, coulombic, hydrophobic (inclusive of hydrogen binding) or chelation type association between mating functional groups of the target ligand and receptor ligand. An example of such functional groups are thiol groups that bond together to form an —S—S— bond.

A coulombic interaction is an ionic interaction between two oppositely charged species. For example, dendrimeric polymers with a positive or negative overall charge may be attracted to a receptor ligand with an opposite charge.

Chelation type associations make use of metal ions such as, but not limited to, the metals Fe, Co, Ni, Ru, Rh, Pd, Os, Ir, Pt, Pb, Sn, Ge, Sc, Y, lanthanides and actinides, B, Al, Ga, In, Tl, Li, Na, K, Rb, Cs, Fr and Be, Mg, Ca, Sr, Ba, Ra and transition metals. Metal ions immobilized onto solid supports such as membrane filters or microparticles may comprise receptor ligands which will chelate with appropriate coordinating groups on the target ligand. An example of a receptor ligand is iminodiacetic acid complexed with $Ni^{2+}$ binds with target ligands that have an affinity for $Ni^{2+}$ acid, such as polyhistidine.

The term "analyte receptor" as used herein refers to any specific binding partner for the analyte and thus may comprise antibodies, antigens, oligonucleotides, peptides, proteins or other species discussed above for the receptor ligand or target ligand.

The term "analyte receptor-target ligand conjugate" as used herein refers to the analyte receptor when conjugated to the target ligand and thus may comprise, for example, a peptide, nucleic acid or combinations of species of analyte receptor referred to above and target ligand referred to above. This term may also refer to the presence of a carrier as described above in relation to the target ligand.

In another aspect of the invention, there is provided assay apparatus comprising a plurality of discrete flow zones characterized in that there is provided an incubation zone upstream of one or more capture zones which only incorporate immobilized receptor ligand which does not bind directly to analyte in use.

The assay apparatus may comprise a lateral strip as shown hereafter in the illustrated embodiment and thus comprise a plurality of discrete flow zones arranged linearly or in end-to-end, overlapping or abutting relationship.

Preferably the assay apparatus also incorporates a wicking chamber for entrapment of liquids after they have passed through the plurality of discrete zones.

More suitably, however, the assay apparatus may comprise a strip of annular form arranged into each of the discrete zones. Advantageously, there is provided a multiplicity of different capture zones with each capture zone having immobilized thereto a different receptor ligand which does not bind directly with analyte in use. Preferably each of the capture zones is separated from each other by incubation zones.

These also may be provided an incubation chamber or vessel which contains the sample and each of the reagents described above. The mixture of sample and reagents may then flow to an initial zone of the assay apparatus before passing though the or each capture zone before passing into the wicking chamber.

The assay apparatus of the invention comprises, in a preferred form, a plurality of filter discs preferably spaced by spacer discs wherein each of the filter discs are contained in a cartridge. The cartridge may be located above the wicking chamber containing wicking material.

It will also be appreciated that the filter discs or annular or linear strips referred to above may be formed from filter material.

Typical filter materials comprise hydrophilic and liquid permeable polymers inclusive of polyvinylidene fluoride, polyamide, polyester cellulose acetate and, nitrocellulose. Use may also be made of fibres formed from polyvinyl chloride, teflon or other fluoropolymers, polysulfone, nylon, polycarbonate, paper, glass, quartz, silica, ceramic or metallic materials or combinations thereof. Use may also be made of wicking materials referred to hereinafter.

The incubation chamber or vessel discussed above may be in the form of wells which are cylindrical, conical, square or other shape dependent upon the requirements of the user. The wells are suitably formed from a substantially rigid, water insoluble, fluid-impervious, thermoplastic material chemically unreactive with assay reagents and samples. Suitable materials include polyvinyl chloride with or without copolymers, teflon or other fluoropolymers, polyethylene, polystyrene, and the like. The preferred material is polystyrene.

Any convenient bibulous absorbent solid material may be formed as the wicking material which allows for capillary transport of liquids from the filter material. Various materials include cellulose particles, silica gel, cellulosic beads, glass fibres, or filter paper. Preferably the wicking material is porous and can be moulded into complex sizes and shapes from thermoplastic polymers including light density polyethylene, ultra high molecular weight polyethylene, polypropylene, polyvinylidene fluoride, polytetrafluoroethylene, nylon, polyethersulfone and ethyl vinyl acetate.

BRIEF DESCRIPTION OF THE DRAWINGS

Reference may now be made to a preferred embodiment of the invention as shown in the attached drawings, wherein.

DETAILED DESCRIPTION OF THE PREFERRED EMBODIMENT

Figure 1:
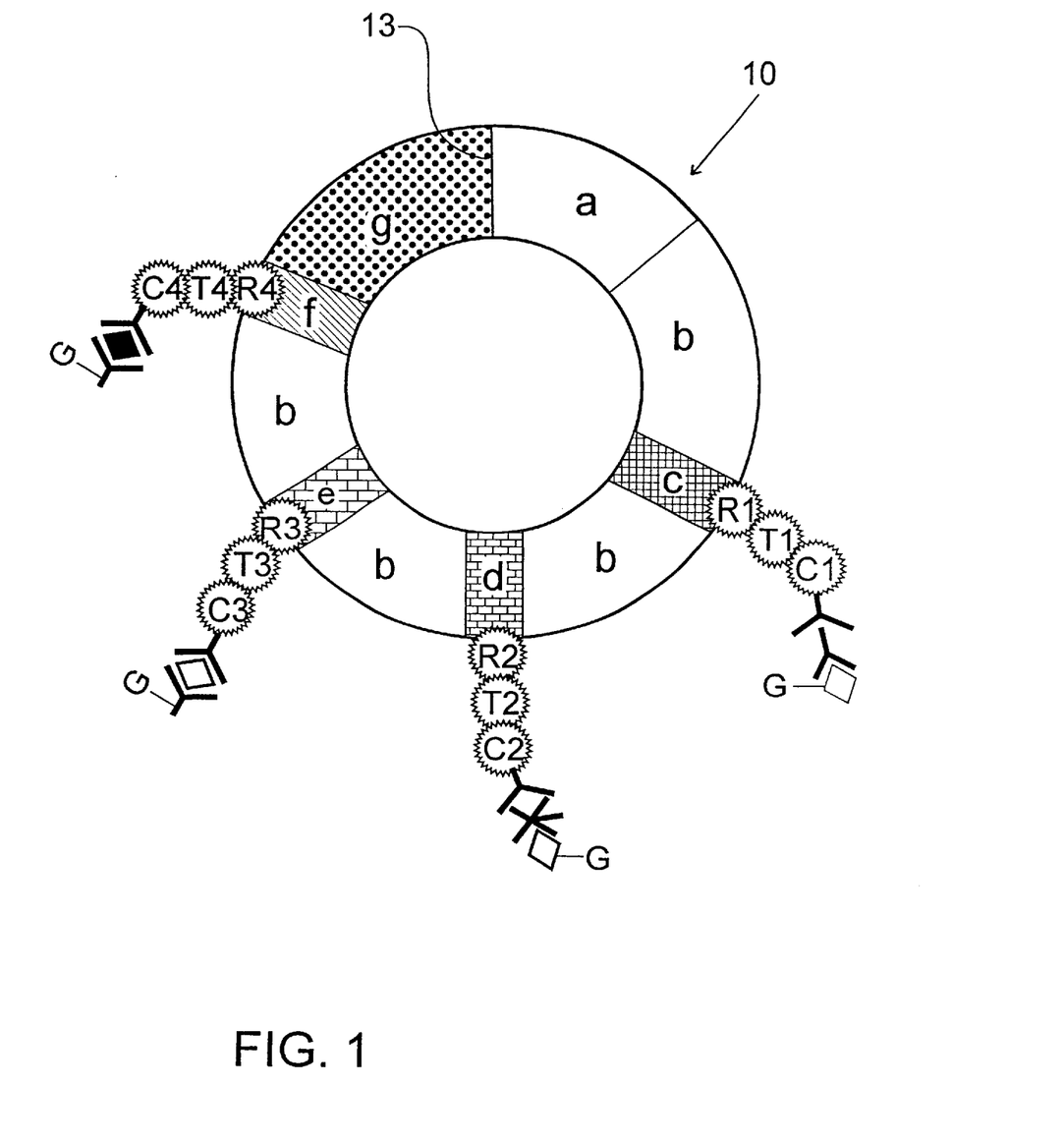
FIG. 1 is a plan view of assay apparatus in the form of a filter disc having a plurality of discrete zones for use in accordance with the invention.

Reference may now be made to FIG. 1 wherein a circular filter assembly 10 can be used in a general sense in conjunction with four different target ligands or molecules (i.e. T1, T2, T3 and T4) and four different carrier molecules (i.e. C1, C2, C3 and C4) so as to provide selective capture of immune complexes in a rapid multi-analyte assay as described hereinafter. The assay of FIG. 1 is a three analyte assay and allows the simultaneous detection of IgM antibodies and IgG antibodies to an infectious agent as well as detection of antigenic component(s) of the infectious agent itself in human blood, serum, saliva, cerebrospinal fluid and other body fluids. It will be noted that the circular filter assembly 10 of FIG. 1 comprises filter zones 10c, 10d and 10e, each of which have been treated with receptor ligand or capture reagent as hereinafter described and which are all relatively narrow compared to filter zones 10a and 10g which do not incorporate capture reagent and incubation zones 10b which are located between zones 10a and 10c, 10c and 10d, 10d and, 10e and 10e and 10f as shown in FIG. 1.

Zones 10c, 10d and 10e are each impregnated with specific receptors ligand R1, R2, R3 and R4 which are able to bind with high affinity target ligands T1–T4 which may be conjugated to carriers C1–C4 such as dendrimers, dendrimeric-type molecules, microparticles, streptavidin, avidin or any other carrier, antibody oligonucleotide or other substance.

Such carriers are capable of conjugation to bio-active agents such as antibodies, peptides and oligonucleotides or molecules mimicking the same. It is also possible to conjugate the target ligands directly to bio-active agents such as antibodies, peptides and oligonucleotides or molecules mimicking the same, eliminating the need to use carriers.

The receptor ligands and target ligands may be small oligonucleotide pairs, small peptides or other organic or non-organic substances which each bind the other with high affinity.

The carriers C1–C4 in this embodiment are conjugated to antibodies directed against human IgG, human IgM and a viral protein. A carrier C4 is also conjugated to antibodies to human albumin which serves as a control.

A sample and the reagent mixture are added successively or concurrently to filter zone 10a initiating flow through filter assembly 10. If the sample is whole blood, zone 10a may be constituted by a blood filter to remove blood cells if desired.

Immune complexes carried on C1 (anti-IgG, IgG antibody from sample and gold labelled antigen) are trapped in filter zone 10c by specific binding of the T1 ligand or molecule on the carrier with the R1 ligand or molecule. This results in accumulation of gold and red banding of filter zone 10c.

Immune complexes carried on C2 (anti-IgM, IgM antibody from sample and gold labelled antigen) are trapped in filter zone 10d by specific binding of the T2 ligand on the carrier with the R2 ligand. This results in accumulation of gold and red banding of filter zone 10d.

Immune complexes carried on C3 (anti-antigen, antigen from sample and gold labelled anti-antigen antibody) are trapped in filter zone 10e by specific binding of the T3 ligand on the carrier C3 with the R3 ligand. This results in accumulation of gold and red banding of filter zone 10d.

Immune complexes carried on C4 (anti-albumin, albumin from sample and gold labelled anti-albumin antibody) are trapped in filter zone 10f by specific binding of the T4 ligand on the carrier C4 with the R4 ligand. This serves as a sample control and demonstrates that (a) sample was added, (b) reagents were added, and (c) indicates how a positive band should appear.

The fluid flow is then directed into filter zone 10g under which is wicking material that draws in the fluid. Flow is physically prevented from re-entering segment 10a by barrier 13.

Figure 2:
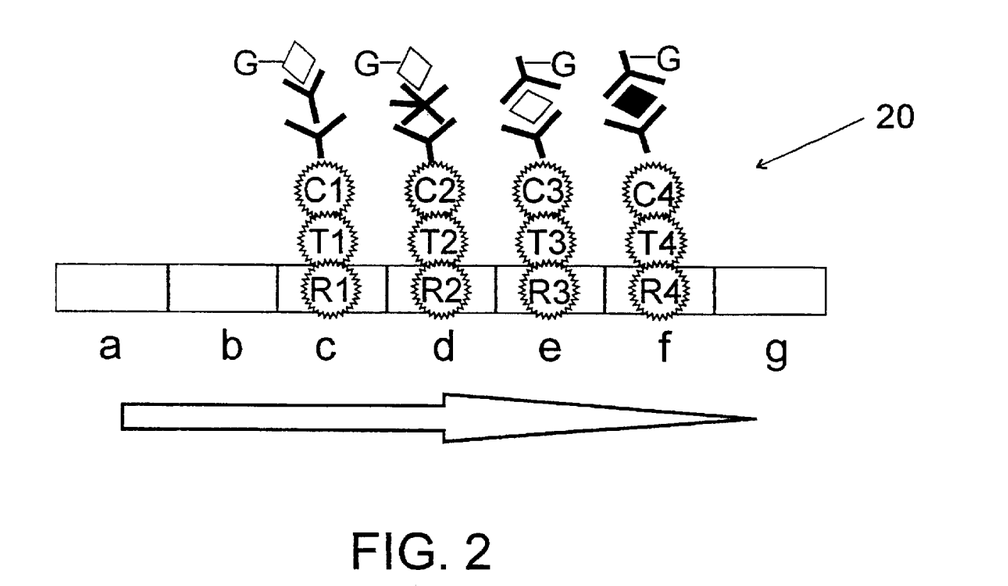
FIG. 2 is a plan of a linear filter strip having a plurality of discrete zones for use with the invention.

Using the same reagents as described in FIG. 1 and the sample fluid, FIG. 2 shows formation of the same complexes to filter zones 20c, 20d, 20e and 20f of a linker filter strip 20. There are also provided incubation zones 20a and 20b and wicking zone 20g.

Figure 3:
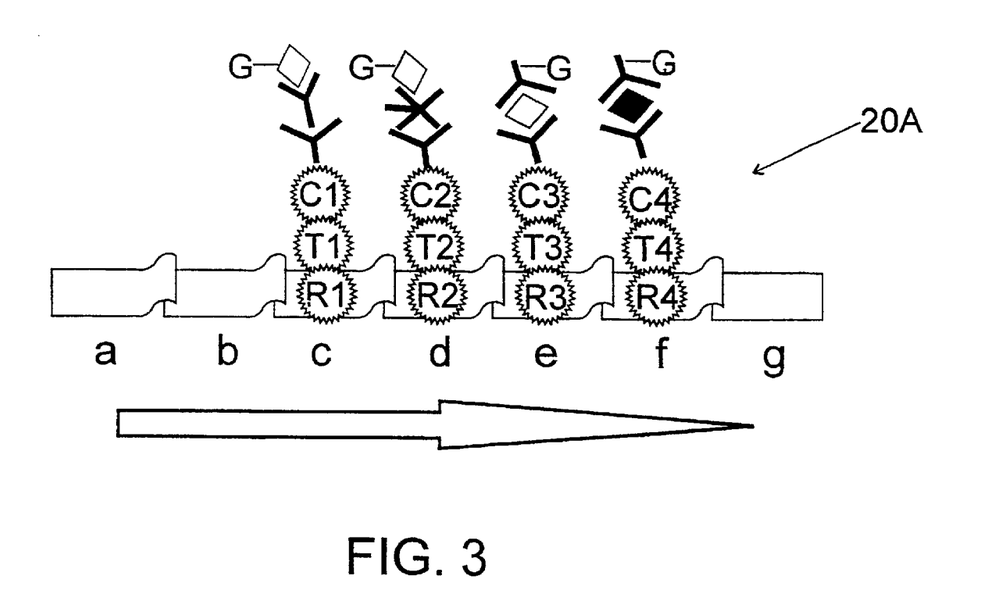
FIG. 3 is a similar view to FIG. 2 but showing an alternative embodiment of linear strip.

Each of the zones 20a through 20f of FIG. 2 may be joined in abutting relationship or overlapping relationship as shown in FIG. 3 in regard to linear filter strip 20A. In another embodiment, each zone 20a through 20f may be connected by linker strips (not shown) or be constituted by an integral strip having receptor ligand(s) applied thereto at one or more spaced locations.

Figure 4:
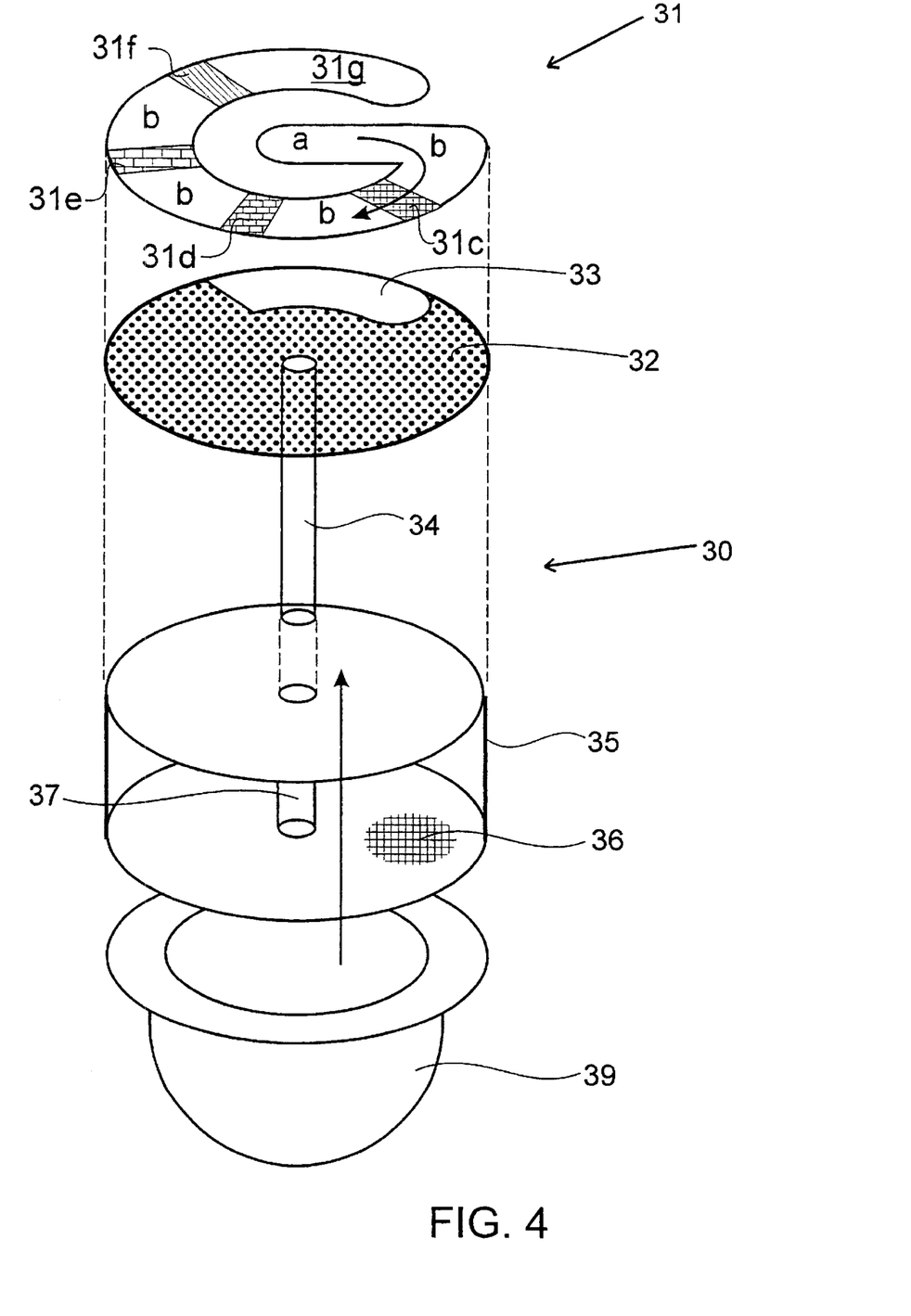
FIG. 4 is an exploded perspective view of assay apparatus in accordance with the invention.

Reference may now be made to another embodiment shown in FIG. 4 wherein filter apparatus 30 comprises a G-shaped filter pad 31 having filter zones 31a, 31b, 31c, 31d, 31e and 31f wherein each of zones 31c, 31d, 31e and 31f has receptor ligand bound thereto. There is also zones 31b which are incubation zones bounding each of zones 31c, 31d and 31e while zone 31f also has zone 31g adjacent thereto.

There is also provided a plastics cover 32 having aperture 33 that mates with filter zone 31g and a capillary tube 34 attached thereto. There is also provided plastics housing 35 containing wicking material 36 which has a central elongate aperture 37 for accommodation of capillary tube 34. There is also provided incubator well 39.

The flow of reagent and sample mixture occurs upwardly from incubation well 39 as shown by the arrows in full outline through capillary tube 34 and into filter zone 31 a and subsequently through each of zones 31c, 31d, 31e and 31f as described in FIG. 1 before being transferred into wicking material 36.

Figure 5:
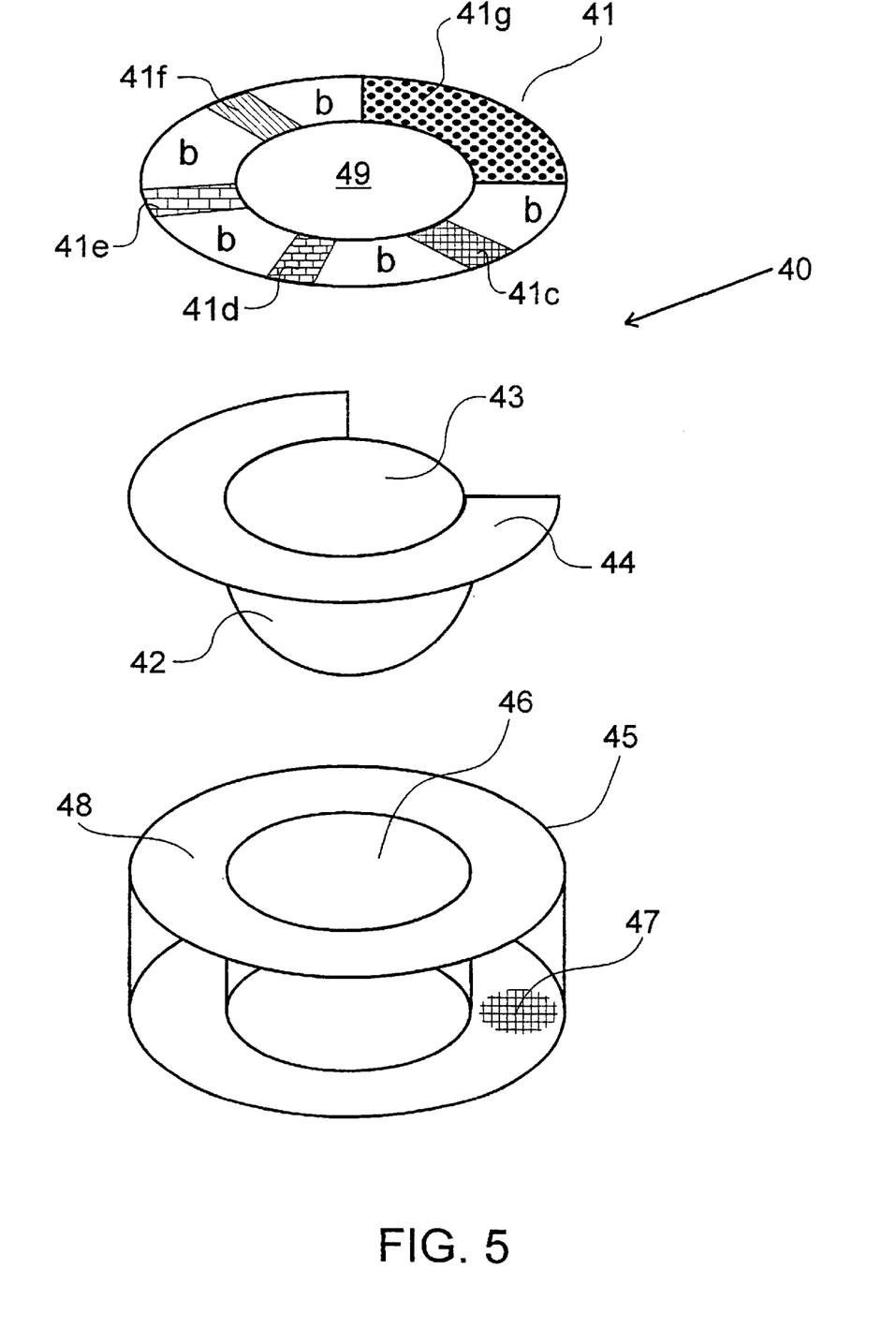
FIG. 5 is an exploded perspective view of assay apparatus in accordance with the invention different to that shown in FIG. 4.

Another embodiment is shown in FIG. 5 wherein reference is made to filter assembly 40 which includes filter pad 41 having incubation zones 41b, zones 41c, 41d, 41e and 41f which incorporate bound receptor ligand and wicking zone 41g. There is also provided a cup 42 formed from plastics material having a slot 43 and a peripheral flange 44 which mates with wicking zone 41g. There is also provided a plastics housing or container 45 having a central recess 46 for retention of cup 42 as shown. Wicking material 47 is located inside container 45 and is exposed to slot 43 through an open top 48 of container 45. There also may be provided a pierceable water resistant or plasticized paper or plastics cover 49 to seal cup 42.

The embodiment of FIG. 5 functions in a similar manner to the FIG. 4 embodiment.

Figure 6:
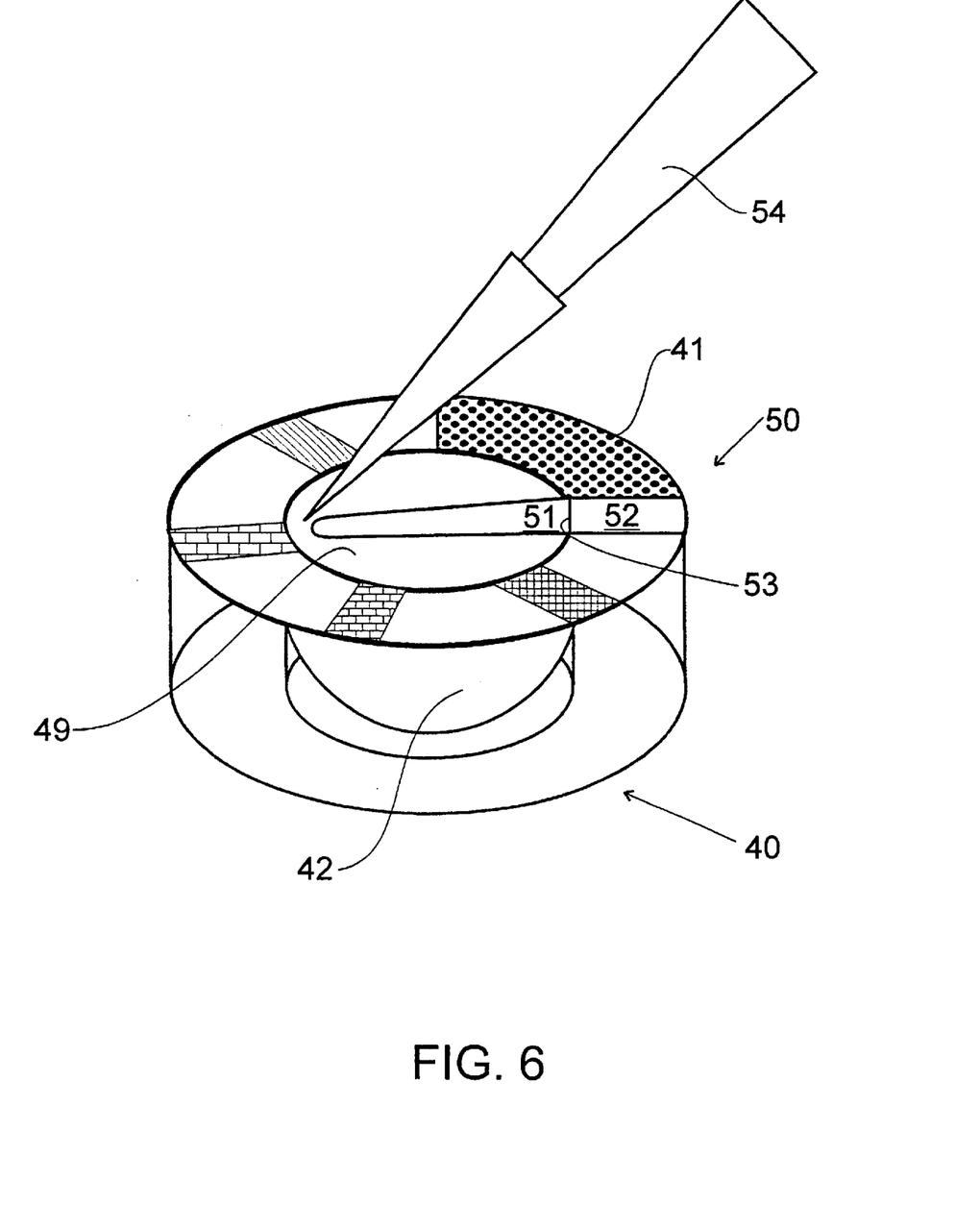
FIG. 6 is a perspective view of assay apparatus shown in FIG. 5 incorporating an absorbent paddle for drawing up a mixture of sample and reagents from an incubation chamber into the! assay apparatus.
Figure 7:
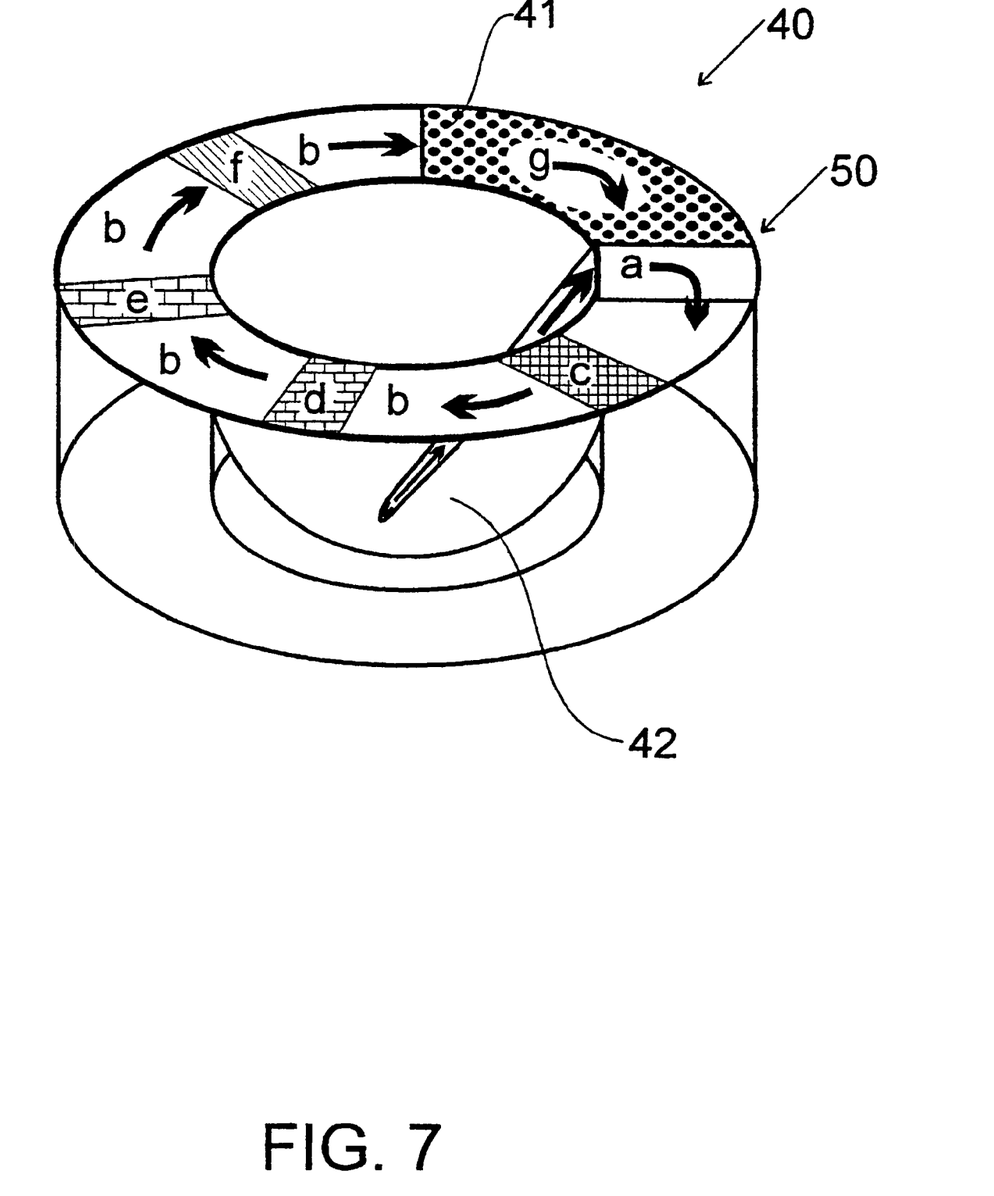
FIG. 7 is a similar view to FIG. 6 showing the absorbent paddle in use.

Reference may now be made to another embodiment shown in FIGS. 6–7 wherein the same filter assembly 40 as discussed in FIG. 5 incorporates an additional component in the form of a paddle 50 in the form of a capillary strip or tube preferably formed from plastics material having an angled shank 51 and support part 52 with a hinge 53 interconnecting shank 51 and support part 52. The paddle 50 is attached to filter assembly 40 as shown in FIG. 6 wherein support part 52 is supported on filter pad 41 and shank 51 is then bent downwardly to penetrate liquid contained in cup or well 42 as shown in FIG. 7.

In use, approximately 50 μl of serum or other suitable sample is pipetted into well 42 by pipette 54 as shown in FIG. 6 which pierces the cover 49 and at the same time pushing the shank 51 into well 42. The serum mixes with a reagent mixture in well 42 and begins to flow up the filter 51 and then into filter zone 41a. The flow of liquid then continues as indicated by the arrows in full outline.

Figure 8:
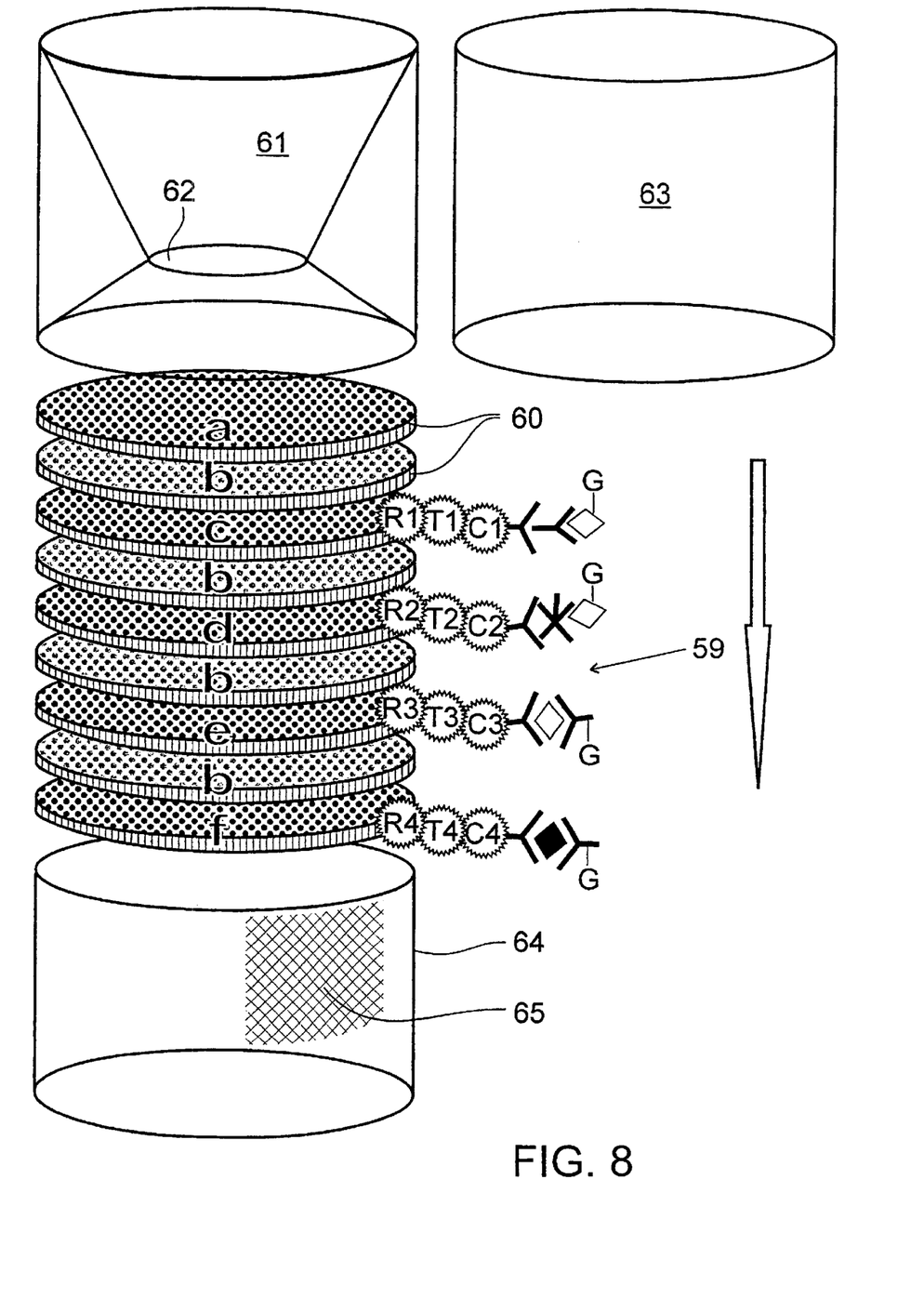
FIG. 8 is an exploded perspective view of another embodiment of assay apparatus in accordance with the invention.

In FIG. 8, reference is made to a filter assembly 59 including a plurality of filter discs 60 which are arranged in a vertical array as shown to facilitate vertical flow of sample and reagents. Each of the filter discs are designated 60a through 60f inclusive as shown and each of filter discs 60c, 60d, 60e and 60f each have incorporated receptor ligand so as to capture various species as already described above in relation to FIG. 1. Filter discs 60b are wicks consisting of polyethylene or other porous material and allow for incubation of the mixture of sample and reagents in its flow down the filter assembly 59. The array of filters may be housed in a housing (not shown) for ease of convenience and there may also be provided frits or spacers (not shown) made from polyethylene or other porous material to allow mixtures of sample and reagents to pass at a controlled rate of passage. Each filter disc may be housed in individual cartridges (not shown) for ease of assembly and removal if desired.

There is also provided an incubation cup or well 61 which may have a restriction 62 to prevent passage of sample and reagents until additional fluid is added. Alternatively, a cup 63 without restriction may be utilized.

The sample may be added to cup 61 or 63 followed immediately by the reagent mixture. Filter 60a may comprise a blood filter to remove blood cells from the mixture if desired. There is also provided container 64 containing wicking material 65.

Figure 9:
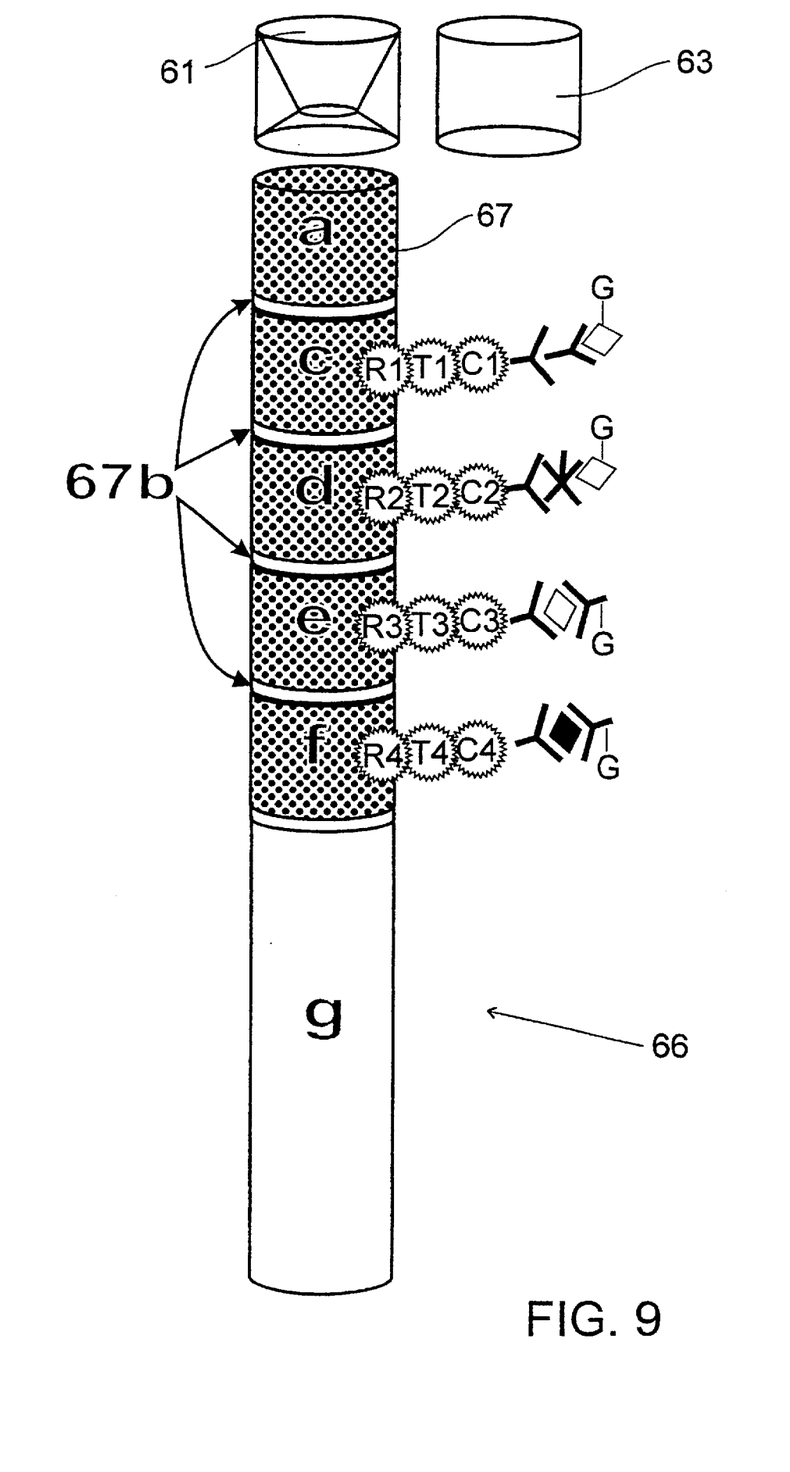
FIG. 9 is a perspective view of another embodiment of assay apparatus in accordance with the invention.

FIG. 9 refers to a filter column 66 comprising successive filters 67a, 67c, 67d, 67e and 67f. These filters are useful for containing microparticles, resins, beads or other particulate matter. Each of these filters are therefore useful in having a receptor ligand attached thereto for the capture of a target substance. Thus, for example, filters 67c, 67d, 67e and; 67f have attached thereto complexes as previously described in FIG. 1. There are also provided frits 67b of porous non-binding material such as polyethylene.

There is also provided wicking module 67g and it will be appreciated that each of modules 67a through 67g may be readily attached to each other through the use of frits 67b. There is also shown the use of wells 61 or 63 as discussed above in FIG. 8.

The filter assembly 66 would be suitable for the testing of water or other liquid samples in which large volumes of sample would need to be passed through the device.

In the case of large volume sample testing, it would be necessary to load the column of filters 67a through 67g with the dendrimer, microparticle or other target labelled carrier, antibody, oligonucleotide, etc. before adding the sample, so as to facilitate capture of the analytes from the sample. After sample addition, the other reagents including gold, enzyme or other labelled detecting agent or tracer is added.

The assay apparatus of the invention has a plurality of uses and may be utilized, for example, as a rapid detection test of multiple pathogens and other substances in environmental, food and clinical samples as well as a replacement test for immunoblot antibody assays used as confirmatory assays, e.g. Hepatitis C and HIV antibodies. Filter assembly 59 and 66 may also be used for testing samples from 1 ml clinical samples to 100 litre samples of water when used in environmental testing.

It is also considered that the invention will, also have special relevance to high throughput screening; of combinatorial chemistry libraries. A combinatorial chemistry library of randomly or non-randomly synthesized oligomers may be prepared on solid support materials such as particles, microparticles, resin beads, and the like with many compositions. Libraries prepared on such particles are used in the art by companies searching for new bioactive compounds such as drugs and for compounds useful as diagnostic agents or vaccines (e.g. synthetic amino acid sequences mimicking discontinuous epitopes derived from micro-organisms such as bacteria and viruses).

The assay apparatus of the invention may be used to incubate such a library of compounds with molecules of interest such as cell surface receptor molecules, enzymes or antibodies. These molecules of interest may be labelled with substances such as enzymes, fluorescent compounds, biotin or other molecules and thus may function as a tracer. Following incubation of the library particles with the labelled tracers, the mixture may be added to incubation well 39, 42, 61 or 63.

The mixture is allowed to pass through the filter and the filter of the invention may be washed to remove unwanted reagents. The aim is to identify those particles bearing oligomers that have bound to the tracer. This can be done by performing an enzyme assay for the presence of the tracer, which will result in a colour change of the labelled particles. If an encoding system was used during the manufacture of the particle library, it may be possible to decode the oligomer identity directly.

Another means of identifying those particles bearing oligomers that have bound to the tracer molecules would be to use tracer molecules conjugated to a specific ligand (e.g. biotin) that will be trapped by a receptor ligand on the filter assembly (e.g. streptavidin). Thus, when the mixtures pass through the filter, particles that have bound the biotinylated tracer molecules will be retained on the filter assembly by biotin-streptavidin binding and all other particles pass through the filter assembly. After washing, the filter assembly will only have on it particles with oligomers that specifically bind to the tracer molecules. Other examples of ligand pairs include oligonucleotide pairs, small peptide binding pairs and metal chelates binding to polyhistidine.

Reference may also be made to test kits constructed in accordance with the invention comprising the abovementioned filter assemblies in the form of linear strip(s), annular strip(s) or filter column(s) together with reagent containers containing target ligand-analyte receptor conjugate(s) and detectable tracer(s). Preferably all of the reagents is accommodated in a single reagent container.

In another aspect of the invention, there is provided assay apparatus in the form of a column of filter members characterized in that there is provided a filter member used for incubation of sample and reagents to facilitate formation of a complex between an analyte and an analyte receptor upstream of one or more filter members used as capture zones.

Advantages applicable to the assay method and apparatus of the invention include:

(1) Because the method and apparatus are independent of analyte, this simplifies the form of packaging that may be utilized in that pre-packaged linear or annular strips or columns could be utilized for a variety of different assays. For example, packages only containing the linear strips may be used in developing countries;

(2) Kits may be marketed in accordance with the invention that include different sets of reagent bottles applicable to different assays together with linear, annular strips or columns. For example, a kit may have multiple different reagent mixture bottles. A first screening bottle may contain Dengue IgM antibody, Japanese encephalitis IgM antibody and malaria IgM antibody reagents. These reagents may be used for an initial screening test. Patients testing negative for all three analytes could be retested using a second set of reagents in a single bottle containing a mixture of reagents for the detection of Dengue virus antigen(s), Japanese encephalitis virus antigen and malaria antigen (s). Patients testing positive for Dengue virus IgM antibody could be retested using a third set of reagents in a single bottle containing a mixture of reagents that differentiated between primary and secondary Dengue virus infection providing for the detection of high level IgG antibody and IgM antibody. For all or any of these procedures, a single universal linear or annular strip or column would be provided. This approach provides for previously unavailable flexibility of use for in vitro diagnostics;

(3) Production of diagnostic kits will be greatly simplified with this invention. Since each analyte or multiple analyte kit does not require manufacture of a filter material impregnated with reagents different from others, a single filter impregnated with one, two, three or more capture zones will serve for the analysis of any analyte or combination or analytes;

(4) The filter media produced for the system should have a greatly extended shelf life as preferentially, nonbiological material or highly stable bio-oligomers will be used for the production of the receptors on the filter media;

(5) Large volumes of sample may be tested with many variants of this system. This will allow greater sensitivity in analyzing samples such as water and other environmental materials for pathogens, chemicals, pollutants and the like. They will also allow the testing of body fluids such as urine in relatively large volumes for the presence of low-level analytes, resulting, in greater test sensitivities and probably earlier detection of analytes in diseases such as leptospirosis and legionellosis in which pathogen specific antigens are excreted in the urine;

(6) Manufacture of the assay apparatus of the invention in the form of strips or columns would be facilitated by manufacture in various arrays commensurate with the relevant utility; and (7) in relation to the assay apparatus of the invention, particularly in the form of filter columns, it will be appreciated that such columns may be reusable.

What is claimed is:

1. A method of assaying for an analyte including the steps of:
   (i) mixing a liquid sample suspected of containing an analyte and reagents comprising a target ligand analyte receptor conjugate incorporating a water soluble carrier for the target ligand and the analyte receptor, which carrier spaces the target ligand from the analyte receptor and a detectable tracer containing a label for the analyte whereby if the analyte is present, there is formed in solution a complex of analyte coupled to the conjugate after incubation of the mixture;
   (ii) passing the mixture through filter apparatus containing a plurality of discrete flow zones wherein at least one zone functions as a capture zone having bonded thereto a receptor ligand for the target ligand;
   (iii) detecting the presence of analyte in the sample by activation of the label in said at least one zone after binding of the complex to the receptor ligand; and
   (iv) continuing the passage of the mixture past said at least one zone to a wicking zone for liquid entrapment.

2. A reagent system for use in the method of claim 1 comprising:
   (i) a conjugate comprising a target ligand and an analyte receptor which incorporates a water soluble carrier for the target ligand and the analyte receptor, which carrier spaces the target ligand from the analyte receptor; and
   (ii) a detectable tracer containing a label for the analyte.

3. A complex formed in the method of claim 1 comprising:
   (i) a conjugate comprising a target ligand and analyte receptor which incorporates a water soluble carrier for the target ligand and the analyte receptor, which carrier spaces the target ligand from the analyte receptor;
   (ii) a detectable tracer carrying a label for the analyte;
   (iii) an analyte binding the label of the detectable tracer and the analyte receptor of the target ligand analyte receptor conjugate; and
   (iv) a receptor ligand bound to a support which binds to the target ligand of the target ligand analyte receptor conjugate.

4. The method as claimed in claim 1 wherein the filter apparatus contains a multiplicity of capture zones each having a different receptor ligand bound thereto and the sample is suspected of containing a multiplicity of analytes and step (ii) comprises passing the mixture comprising the sample and reagents comprising a target ligand-analyte receptor conjugate specific for each analyte and a detectable tracer containing a label for each analyte through the filter apparatus and step (iii) comprises detecting the presence of each analyte by activation of the label in each capture zone after bonding of each complex to its associated receptor ligand.

5. The method as claimed in claim 4 wherein there is provided an incubation chamber adjacent said filter apparatus for incubation of the sample and reagents prior to being passed through the filter assembly.

6. The method as claimed in claim 4 wherein the mixture is incubated in an incubation zone or zones of the filter apparatus prior to passage through said at least one zone.

7. The method as claimed in claim 1 wherein there is provided an incubation chamber adjacent said filter apparatus for incubation of the sample and reagents prior to being passed through the filter assembly.

8. The method as claimed in claim 1 wherein the mixture is incubated in an incubation zone or zones of the filter apparatus prior to passage through said at least one zone.

9. The method as claimed in claim 1 wherein the sample and reagents after passing through the filter apparatus are then passed into a wicking chamber containing wicking material.

10. The method as claimed in claim 1 wherein wicking zone is a zone of the filter apparatus downstream of said at least one zone.

11. The method as claimed in claim 1 wherein the analyte is selected from the group consisting of antibodies, antigens, immunoglobulins IgA, IgG, IgE, IgM, nucleic acids, and proteins.

12. The method as claimed in claim 1 wherein the label is a binding partner for the analyte incorporating coloured particles, coloured dendrimers or coloured dendrimeric-type polymers.

13. The method as claimed in claim 12 wherein the coloured particles are colloidal gold.

14. The method as claimed in claim 1 wherein the receptor ligand is selected from the group consisting of haptens, oligonucleotides, peptides and oligomers.

15. The method as claimed in claim 14 wherein the target ligand is selected from the group consisting of haptens, oligonucleotides, peptides and oligomers.

16. The method as claimed in claim 1 wherein the carrier is selected from the group consisting of dendrimers, dendrimeric-type polymers, polymers, branched polymers, microparticles, latex beads, and oligomers.

17. The method as claimed in claim 16 wherein the microparticles has an average individual size of 0.01–50 microns.

18. The method as claimed in claim 17 wherein the microparticles are selected from the group consisting of polystyrene, polymethylacrylate, polypropylene, silica, teflon and other fluoropolymers, latex, polytetrafluoroethylene, polyacrylanitrile and polycarbonate.

* * * * *